United States Patent
Gao et al.

(10) Patent No.: US 11,772,038 B2
(45) Date of Patent: Oct. 3, 2023

(54) METHODS FOR OPTIMIZING GAS UTILIZATION

(71) Applicant: LanzaTech, Inc., Skokie, IL (US)

(72) Inventors: Allan Haiming Gao, Skokie, IL (US); Robert John Conrado, Skokie, IL (US); Sebastian Michal Bernasek, Skokie, IL (US); Michael Anthony Schultz, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 301 days.

(21) Appl. No.: 16/901,546

(22) Filed: Jun. 15, 2020

(65) Prior Publication Data

US 2021/0008486 A1    Jan. 14, 2021

Related U.S. Application Data

(60) Provisional application No. 62/872,869, filed on Jul. 11, 2019.

(51) Int. Cl.
| | |
|---|---|
| *A23K 10/12* | (2016.01) |
| *C12P 7/14* | (2006.01) |
| *C12P 7/08* | (2006.01) |
| *B01D 53/84* | (2006.01) |
| *B01D 53/047* | (2006.01) |
| *C12P 7/06* | (2006.01) |
| *C12P 7/54* | (2006.01) |

(52) U.S. Cl.
CPC ........... *B01D 53/047* (2013.01); *B01D 53/84* (2013.01); *C12P 7/065* (2013.01); *C12P 7/14* (2013.01); *C12P 7/54* (2013.01); *B01D 2257/108* (2013.01)

(58) Field of Classification Search
CPC .... C12P 7/14; C12P 7/065; C12P 7/08; C12R 1/145; C12R 1/02; A23K 10/12
See application file for complete search history.

(56) References Cited

U.S. PATENT DOCUMENTS

| | | | |
|---|---|---|---|
| 11,549,103 B2* | 1/2023 | Nagaraju | C12N 9/0006 |
| 2012/0301934 A1 | 11/2012 | Schultz et al. | |
| 2013/0143972 A1 | 6/2013 | Townsend et al. | |
| 2014/0370559 A1 | 12/2014 | Oakley et al. | |
| 2015/0247171 A1 | 9/2015 | Schultz | |
| 2019/0078121 A1* | 3/2019 | Conrado | C12N 1/20 |
| 2020/0248152 A1* | 8/2020 | Nagaraju | C12P 7/54 |

FOREIGN PATENT DOCUMENTS

| | | |
|---|---|---|
| WO | 2007/117157 A1 | 10/2007 |
| WO | 2008/115080 A1 | 9/2008 |
| WO | 2009/151342 A1 | 12/2009 |
| WO | 2011/112103 A1 | 9/2011 |
| WO | 2012/024522 A2 | 2/2012 |
| WO | 2012/026833 A1 | 3/2012 |
| WO | 2012/053905 A1 | 4/2012 |
| WO | 2012-054798 A2 | 4/2012 |
| WO | 2012-058508 A2 | 5/2012 |
| WO | 2012/115527 A2 | 8/2012 |
| WO | 2013/036147 A2 | 3/2013 |
| WO | 2013/180581 A1 | 12/2013 |
| WO | 2013/180584 A1 | 12/2013 |
| WO | 2013/185123 A1 | 12/2013 |
| WO | 2013/191567 A1 | 12/2013 |
| WO | 2014/036152 A1 | 3/2014 |
| WO | 2016/094334 A1 | 6/2016 |
| WO | 2016/191625 A1 | 12/2016 |
| WO | 2017/0066498 A1 | 4/2017 |
| WO | 2019-051069 A1 | 3/2019 |
| WO | 2019/126400 A1 | 6/2019 |

OTHER PUBLICATIONS

Chiba, Section 18: Diet Formulation and Common Feed Ingredients, Animal Nutrition Handbook, 3rd revision, 2014, pp. 575-633.
Ragsdale, Biochim Biophys Acta, 2008, pp. 1873-1898, vol. 1784.
International Search Report and Written Opinion issued in corresponding International Application No. PCT/US2020/037729, dated Sep. 24, 2020, 15 pages.
Chen, Wei-Hsin et al, "An evaluation of hydrogen production from the perspective of using blast furnace gas and coke oven gas as feedstocks", International Journal of Hydrogen Energy, 36(18), pp. 11727-11737, Jul. 20, 2011 (Jul. 20, 2011).

* cited by examiner

*Primary Examiner* — Maryam Monshipouri (57) ABSTRACT

The invention provides for the optimal utilization of gas by a fermentation process, whereby the various components within the gas stream are separated to increase the efficiency of the microorganisms. The invention is capable of tailoring the composition of the gas being used by the fermentation process so as to enhance the production of various products. The invention is capable of applying such controlled separation and utilization of gas to produce different products in two parallel fermentation processes. The invention is also capable of applying such controlled separation and utilization of gas to produce one product in a first fermentation process, which may be converted to a different product in a second fermentation process. The invention is additionally capable of mitigating culture inhibition.

13 Claims, 3 Drawing Sheets

METHODS FOR OPTIMIZING GAS UTILIZATION

CROSS-REFERENCE TO RELATED APPLICATIONS

The application claims the benefit of U.S. Provisional Application No. 62/872,869 filed Jul. 11, 2019, the contents of which are hereby incorporated by reference.

FIELD OF THE INVENTION

The invention relates to methods for optimizing the utilization of gas by a fermentation process. In particular, the invention relates to the controlled separation and use of various components within a gas stream so as to maximize the production of certain products and overall carbon capture efficiency of the process.

BACKGROUND OF THE INVENTION

Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). Reduction of greenhouse gas emissions, particularly $CO_2$, is critical to halt the progression of global warming and the accompanying shifts in climate and weather. Conversion of such gas emissions to one or more fuel or chemical is one potential solution to reduce emissions.

It has long been recognized that catalytic processes, such as the Fischer-Tropsch process, may be used to convert gases comprising carbon dioxide ($CO_2$), carbon monoxide (CO), and/or hydrogen ($H_2$) into a variety of fuels and chemicals. Recently, however, gas fermentation has emerged as an alternative platform for the biological fixation of such gases. In particular, C1-fixing microorganisms have been demonstrated to convert gases comprising $CO_2$, CO, $CH_4$, and/or $H_2$ into products such as ethanol and 2,3-butanediol.

Such gases may be derived, for example, from industrial sources, including gas from carbohydrate fermentation, gas from cement making, pulp and paper making, steel making, oil refining and associated processes, petrochemical production, coke production, anaerobic or aerobic digestion, gasification (derived from sources including but not limited to biomass, liquid waste streams, solid waste streams, municipal streams, fossil resources including natural gas, coal and oil), natural gas extraction, methane reformation, oil extraction, metallurgical processes, for production and/or refinement of aluminium, copper, and/or ferroalloys, geological reservoirs, and catalytic processes (derived from steam sources including but not limited to steam methane reforming, steam naphtha reforming, petroleum coke gasification, catalyst regeneration—fluid catalyst cracking, catalyst regeneration-naphtha reforming, and dry methane reforming).

Gas fermentation has a variety of advantages over the Fischer-Tropsch process. Firstly, Fischer-Tropsch utilizes high temperatures (150-350° C.), elevated pressures (30 bar), and heterogeneous catalysts such as cobalt, ruthenium, and iron. In comparison, gas fermentation takes places at about 37° C. and can be conducted at atmospheric pressure, which presents significant energy and cost savings relative to the Fischer-Tropsch process. Additionally, the Fischer-Tropsch process requires a relatively fixed $H_2$:CO ratio in the syngas, around 2:1, whereas gas fermentation is capable of receiving and utilizing a diverse range of substrates with varying $H_2$:CO ratios.

Depending on the source of the gas stream and the operation of the upstream industrial source, the $H_2$:CO ratio may vary greatly. Although gas fermentation is capable of receiving and utilizing a diverse range of substrates with varying $H_2$:CO ratios, certain compositions of gas may be more ideal than others to produce certain desired products. For instance, certain products may be optimally produced from gas streams with lower $H_2$:CO ratios.

However, no matter what the desired product may be, one major objective of the gas fermentation process is to maximize the overall carbon capture achieved by the process. Depending on the $H_2$:CO ratio of the gas stream, the fermentation process may, as a by-product, produce $CO_2$ in the course of generating a fermentation product. The conversion of carbon monoxide into carbon dioxide can be seen as a reduction in carbon capture efficiency as the carbon monoxide should ideally be converted to one or more fuel and/or chemical instead of carbon dioxide.

Accordingly, there remains a need for a method that enables the modification of the composition of the gas such that the gas is optimized for producing certain products all while maximizing the overall carbon capture efficiency of the process.

BRIEF SUMMARY OF THE INVENTION

The invention provides a method for the optimizing the utilization of gas by a fermentation process. Specifically, the method enables the modification of the composition of gas such that the gas is optimized for producing certain products in one or more fermentation process while also maximizing the overall carbon capture efficiency of the process. In particular embodiments, the invention utilizes two fermentation processes in parallel with one another. Preferably, when two fermentation processes are utilized, the gas stream is separated into a hydrogen rich stream and a hydrogen depleted stream using at least one separation module. At least a portion of the hydrogen rich stream is fermented in a first fermentation process using at least a first reactor comprising a liquid nutrient medium containing a culture of one or more C1-fixing microorganism to produce a first fermentation product. At least a portion of the hydrogen depleted stream is fermented in a second fermentation process using at least a second reactor comprising a liquid nutrient medium containing a culture of one or more C1-fixing microorganism to produce a second fermentation product. In certain instances, the first fermentation product and the second fermentation product are different products. For example, in one embodiment the first fermentation product is ethanol and the second fermentation product is 2,3-butandediol.

In certain instances the $H_2$:CO ratio of the hydrogen rich gas is 5:1, or greater than 5:1. In various embodiments, the $H_2$:CO ratio of the hydrogen rich gas is between 2:1 and 5:1. For example, the $H_2$:CO ratio of the hydrogen rich gas may be between 2:1 and 3:1, between 2.5:1 and 3.5:1, between 3:1 and 4:1, between 3.5:1 and 4.5:1, between 2:1 and 4:1, between 2.5:1 and 4.5:1, or between 2.5:1 and 5:1. Preferably, the hydrogen rich gas has a higher $H_2$:CO ratio than the hydrogen depleted gas.

Preferably, the first fermentation process utilizes the hydrogen rich gas to produce at least one fermentation product selected from the group consisting of ethanol, acetate, monoethylene glycol (MEG), 1,2-propanediol, acetone, isopropanol, lactate, 1,3-butanediol, 2-butanol, 2-hydroxyisobutyric acid, 3-hydroxybutyrate, methyl ethyl ketone (MEK), terpenes including isoprene, adipic acid, 1-hexanol, and 1-octanol.

In certain instances the $H_2$:CO ratio of the hydrogen depleted gas is 0.1:1, or less than 0.1:1. In various embodiments, the $H_2$:CO ratio of the hydrogen depleted gas is between 0.1:1 and 2:1. For example, the $H_2$:CO ratio of the hydrogen depleted gas may be between 0.05:1 and 1.5:1, between 0.05:1 and 2:1, between 0.2:1 and 1.5:1, between 0.2:1 and 2:1, between 0.5:1 and 1.5:1, or between 0.5:1 and 2:1. Preferably, the hydrogen depleted gas has a lower $H_2$:CO ratio than the hydrogen rich gas.

Preferably, the second fermentation process utilizes the hydrogen depleted gas to produce at least one fermentation product selected from the group consisting of ethanol, acetate, monoethylene glycol (MEG), 1,2-propanediol3-hydroxypropionate, acetone, isopropanol, lactate, 1,3-butanediol, 2-butanol, 2-hydroxyisobutyric acid, 3-hydroxybutyrate, methyl ethyl ketone (MEK), isoamyl alcohol, terpenes including isoprene, adipic acid, 1-hexanol, 1-octanol, and chorismate-derived products. In certain instances, it is more advantageous to produce certain products with the hydrogen depleted stream instead of the hydrogen rich stream. For example, 3-hydroxypropionate, isoamyl alcohol, and/or chorismate-derived products, are preferably produced using the hydrogen depleted stream instead of the hydrogen rich stream.

In various instances where the invention utilizes two fermentation processes, gas and liquid nutrient medium may be flowed in parallel to both the first fermentation process and the second fermentation process.

In certain instances the hydrogen separation module is comprised of at least one pressure swing adsorption process. In various embodiments, the hydrogen separation module may include at least one separation technique selected from the group consisting of pressure swing adsorption, temperature swing adsorption, membrane separation, or any other gas separation technique used to adjust the composition of the gas by selective removal of one or more of CO, $H_2$, and/or $CO_2$. Preferably, the hydrogen separation module is capable or separating at least a seventy-five percent (75%) of the hydrogen from the gas stream so as to produce a hydrogen rich stream and a hydrogen depleted gas stream. In certain instances, the hydrogen separation module separates at least ninety-five percent (95%) of the hydrogen from the gas stream so as to produce a hydrogen rich gas stream and a hydrogen depleted gas stream. In various instances, both the hydrogen rich gas stream and the hydrogen depleted gas stream contain some amount of carbon monoxide and/or carbon dioxide.

Preferably the gas stream is sourced from one or more industrial source selected from the group consisting of carbohydrate fermentation, gas fermentation, cement making, pulp and paper making, steel making, oil refining and associated processes, petrochemical production, coke production, anaerobic or aerobic digestion, gasification, natural gas extraction, methane reformation, oil extraction, metallurgical processes, for production and/or refinement of aluminium, copper, and/or ferroalloys, geological reservoirs, and catalytic processes. In certain instances, at least a portion of the gas is derived from a methane reformation process. Such methane reformation process preferably converts at least a portion of a methane-containing gas into a gas stream comprising at least a portion of carbon monoxide and hydrogen. In certain embodiments, the methane is sourced from fossil fuel production facilities, landfills, and/or wastewater treatment facilities.

In various embodiments at least a portion of the gas stream is comprised of a blast furnace top gas from a metallurgical process.

The optimization of the gas may also include the mixing of one or more additional gas to arrive at a suitable $H_2$:CO ratio. For example, this additional gas may be sourced from one or more electrolysis process (including both electrolysis processes for producing hydrogen from water and/or electrolysis process for producing carbon monoxide from carbon dioxide), industrial source, methane reformation process, and/or vent gas from the fermentation process. However, in various embodiments, the invention does not utilize the mixing of one or more additional gases, and instead solely utilizes the separation of components from the gas stream by the hydrogen separation module.

In certain instances, at least a portion of the vent gas produced in the first fermentation process is recycled to the hydrogen rich stream.

In certain instances at least a portion of the vent gas produced in the second fermentation process is recycled to the hydrogen depleted stream.

To ensure the ideal mixing of the vent gas from the fermentation process with the gas from the industrial source, at least a portion of the vent gas may be passed through at least one hydrogen separation module. In certain instances, at least a portion of the vent gas produced in the first fermentation process is passed through a pressure swing adsorption process prior to being recycled to the hydrogen rich stream. In certain instances, at least a portion of the vent gas produced in the second fermentation process is passed through a pressure swing adsorption process prior to being recycled to the hydrogen depleted stream.

Preferably, the fermentation processes utilize at least one C1-fixing microorganism. In certain instances, both the first fermentation process and the second fermentation process utilize the same species of C1-fixing microorganism. In other embodiments, the first fermentation process utilizes a different species of microorganism than the second fermentation process. Preferably, the C1-fixing microorganism(s) used in the fermentation processes is selected from the group consisting of *Moorella, Clostridium, Ruminococcus, Acetobacterium, Eubacterium, Butyribacterium, Oxobacter, Methanosarcina*, and *Desulfotomaculum*. In certain instances, both the first fermentation process and the second fermentation process utilize a C1-fixing microorganism from the genus *Clostridium*. Such microorganism utilized by the first fermentation process and the second fermentation process is preferably *Clostridium autoethanogenum*.

In particular embodiments, the invention utilizes two fermentation processes in series with one another. Preferably, when two fermentation processes are used in series with one another, the gas stream is separated into a hydrogen rich stream and a hydrogen depleted stream using at least one hydrogen separation module. At least a portion of the hydrogen rich stream being fermented in a first fermentation process using at least one reactor comprising a liquid nutrient medium containing a culture of one or more C1-fixing microorganism to produce a first fermentation product. At least a portion of the hydrogen depleted stream being fermented in a second fermentation process containing a culture of one or more C1-fixing microorganism to produce a second fermentation product. When the two fermentation processes are in series with one another, preferably at least a portion of the first fermentation product is passed to the second fermentation process to produce the second fermentation product.

In certain instances, the first fermentation product is acetic acid. Preferably, when the fermentation processes are in series, at least a portion of the acetic acid from the first fermentation process is converted to ethanol in the second fermentation process.

In particular embodiments, the invention encompasses one fermentation process which recycles at least a portion of the vent gas stream to optimize the composition of the gas stream for producing a fermentation product. Such fermentation process preferably ferments at least a portion of a gas stream from an industrial source using at least one reactor comprising a liquid nutrient medium containing a culture of one or more C1-fixing microorganism to produce a fermentation product and a vent gas stream. At least a portion of the vent gas stream may be recycled to the bioreactor, which in some instances can reduce and/or mitigate the potential inhibition of the culture.

In certain instances at least a portion of the vent gas is passed through a pressure swing adsorption process prior to being recycled to the bioreactor.

The use of the pressure swing adsorption process preferably removes at least one component selected from the group consisting of carbon dioxide, inorganic hydrocarbons, tars, organic nitrogen, and organic and inorganic sulfur from the vent gas stream to create a clarified vent gas stream.

Preferably the pressure swing adsorption process simultaneously removes at least a portion of at least two components selected from the group consisting of carbon dioxide, inorganic hydrocarbons, tars, organic nitrogen, and organic and inorganic sulfur from the vent gas stream to create a clarified vent gas stream.

In various instances, the total gas stream being sent to the fermentation process is comprised of a combination of the gas stream from the industrial source and at least a portion of the clarified vent gas.

The clarified vent gas preferably contains higher proportions of methane and nitrogen when compared to the composition of the gas from the industrial source.

In certain embodiments where the clarified vent gas is recycled to the fermentation process, the recycling of the clarified vent gas to the bioreactor of the fermentation process increases the overall composition of methane and nitrogen in the total gas stream by at least fifteen percent (15%). In certain instances, the recycling of at least a portion of the clarified vent gas to the bioreactor increases an overall composition of methane and nitrogen in the total gas stream by at least fifty percent (50%). In certain instances, the recycling of at least a portion of the clarified vent gas to the bioreactor increases an overall composition of methane and nitrogen in the total gas stream between ten and twenty percent (10-20%), between fifteen and thirty percent (15-30%), between twenty-five and thirty-five percent (25-35%), between thirty and forty-five percent (30-45%), or between fifteen and fifty percent (15-50%). Preferably the recycling of at least a portion of the clarified vent gas to the bioreactor reduces and/or mitigates the potential inhibition of the culture.

In various instances the fermentation process utilizes at least a portion of the total gas stream to produce one or more fuels or chemicals. At least one of the products produced by the fermentation process may be selected from the group consisting of ethanol, acetate, monoethylene glycol (MEG), 1,2-propanediol, 1-propanol, 3-hydroxypropionate, acetone, isopropanol, lactate, 1,3-butanediol, 2-butanol, 2-hydroxy-isobutyric acid, 3-hydroxybutyrate, methyl ethyl ketone (MEK), isoamyl alcohol, terpenes including isoprene, adipic acid, 1-hexanol, 1-octanol, and chorismate-derived products.

The one or more fermentation processes, as part of producing the one or more fuels or chemicals, produce microbial biomass. At least a portion of the microbial biomass produced by the one or more fermentation processes may be converted to a single cell protein (SCP).

The one or more fuels or chemicals may, in some embodiments, be sent to a secondary conversion processes. In various instances, the secondary conversion process further converts at least a portion of one or more fuels or chemicals to at least one component of diesel fuel, jet fuel, gasoline, propylene, nylon 6-6, rubber, and/or resins.

DETAILED DESCRIPTION OF THE INVENTION

The inventors have identified that by controlling the composition of the gas being fed to one or more fermentation process, selectivity toward a desired product can be improved. The inventors found one mechanism to control the composition is to utilize two fermentation processes alongside one another.

Definitions

Unless otherwise defined, the following terms as used throughout this specification are defined as follows:

The term "fermentation", "gas fermentation" and the like should be interpreted as the process which receives one or more substrate, such as syngas produced by gasification and produces one or more product through the utilization of one or more C1-fixing microorganism. Preferably the fermentation process includes the use of one or more bioreactor. The fermentation process may be described as either "batch" or "continuous". "Batch fermentation" is used to describe a fermentation process where the bioreactor is filled with raw material, e.g. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. Preferably the fermentation process is continuous.

Unless the context requires otherwise, the phrases "fermenting", "fermentation process" or "fermentation reaction" and the like, as used herein, are intended to encompass both the growth phase and product biosynthesis phase of the gaseous substrate.

In certain embodiments, the fermentation is performed in the absence of carbohydrate substrates, such as sugar, starch, lignin, cellulose, or hemicellulose.

The terms "increasing the efficiency", "increased efficiency" and the like, when used in relation to a fermentation process, include, but are not limited to, increasing the amount of carbon captured by the process, decreasing the amount of carbon converted to one or more undesired by-product, increasing one or more of the rate of growth of microorganisms catalysing the fermentation, the growth and/or product production rate at elevated product concentrations, increasing the volume of desired product produced per volume of substrate consumed, increasing the rate of production or level of production of the desired product, increasing the relative proportion of the desired product produced compared with other by-products of the fermentation, decreasing the amount of water consumed by the process, and decreasing the amount of energy utilized by the process.

In particular embodiments, the presence of hydrogen results in an improved overall efficiency of ethanol production by the fermentation process.

Operating the fermentation process in the presence of hydrogen has the added benefit of reducing the amount of $CO_2$ produced by the fermentation process. For example, a gaseous substrate comprising minimal $H_2$ will typically produce ethanol and $CO_2$ by the following stoichiometry [$6CO+3H_2O \rightarrow C_2H_5OH+4CO_2$]. As the amount of hydrogen utilized by the C1-fixing bacterium increases, the amount of $CO_2$ produced decreases [e.g., $2CO+4H_2 \rightarrow C_2H_5OH+H_2O$].

At a stoichiometric ratio of 2:1 ($H_2$:CO), $CO_2$ production is completely avoided. As shown below, at varying stoichiometric ratios of $H_2$:CO varying amounts of carbon are not adequately utilized and instead of being converted to ethanol, they are converted to $CO_2$ by-product.

$5CO+1H_2+2H_2O \rightarrow C_2H_5OH+3\ CO_2 (\Delta G° = -204.80$ kJ/mol ethanol)

$4CO+2H_2+1H_2O \rightarrow 1C_2H_5OH+2CO_2 (\Delta G° = -184.70$ kJ/mol ethanol)

$3CO+3H_2 \rightarrow 1C_2H_5OH+1CO_2 (\Delta G° = -164.60$ kJ/mol ethanol)

"Stream" refers to any substrate which is capable of being passed, for example, from one process to another, from one module to another, and/or from one process to a carbon capture means.

A "hydrogen rich stream" is a gas stream which has a higher relative proportion of hydrogen than a "hydrogen depleted stream". In various instances the hydrogen rich stream has a $H_2$:CO stoichiometric ratio of at least 2:1, whereas the hydrogen depleted stream has a $H_2$:CO stoichiometric ratio of less than 2:1.

The term "clarified gas", "clarified stream" and the like refers to the gas stream that has been passed through at least one hydrogen separation module.

"Hydrogen separation module" include at least one separation technique selected from the group consisting of pressure swing adsorption, temperature swing adsorption, membrane separation, or any other gas separation technique used to adjust the composition of the gas by selective removal of one or more of CO, $H_2$, and/or $CO_2$. Preferably, the hydrogen separation module comprises at least one pressure swing adsorption process. In various instances the hydrogen separation module is used to simultaneously remove at least two components selected from the group consisting of carbon dioxide, inorganic hydrocarbons, tars, organic nitrogen, and organic and inorganic sulfur.

The term "carbon capture" as used herein refers to the sequestration of carbon compounds including $CO_2$ and/or CO from a gas stream comprising $CO_2$ and/or CO and either:
converting the $CO_2$ and/or CO into products; or
converting the $CO_2$ and/or CO into substances suitable for long-term storage; or
trapping the $CO_2$ and/or CO in substances suitable for long-term storage;
or a combination of these processes.

The term "bioreactor", "reactor" and the like includes a device capable of being used for a fermentation process. A bioreactor may consist of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The reactor is preferably adapted to receive a gaseous substrate comprising CO or $CO_2$ or $H_2$ or mixtures thereof. A fermentation process may comprise multiple reactors (stages), either in parallel or in series. For example, the fermentation process may comprise a first growth reactor in which the bacteria are cultured and a second fermentation reactor, to which fermentation broth from the growth reactor may be fed and in which most of the fermentation products may be produced.

The term "fermentation broth" or "broth" is intended to encompass the mixture of components including nutrient media and a culture or one or more microorganisms. Preferably the fermentation process utilizes fermentation broth to ferment the gas stream to one or more product.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium.

"Nutrient media" or "Nutrient medium" is used to describe bacterial growth media. Preferably the fermentation process utilizes nutrient medium within the bioreactor. Generally, this term refers to a media containing nutrients and other components appropriate for the growth of a microbial culture. The term "nutrient" includes any substance that may be utilized in a metabolic pathway of a microorganism. Exemplary nutrients include potassium, vitamins, trace metals, and amino acids.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "desired composition" is used to refer to the desired level and types of components in a substance, such as, for example, of a gas stream. More particularly, a gas is considered to have a "desired composition" if it contains a particular component (e.g. CO, $H_2$, and/or $CO_2$) and/or contains a particular component at a particular proportion and/or does not contain a particular component (e.g. a contaminant harmful to the microorganisms) and/or does not contain a particular component at a particular proportion. More than one component may be considered when determining whether a gas stream has a desired composition.

A "microorganism" is a microscopic organism, especially a bacterium, archea, virus, or fungus. The microorganism of the invention is typically a bacterium. As used herein, recitation of "microorganism" should be taken to encompass "bacterium." It should be noted that the term microorganism and the term bacteria are used interchangeably throughout the document.

A "parental microorganism" is a microorganism used to generate a microorganism of the invention. The parental microorganism may be a naturally-occurring microorganism (e.g., a wild-type microorganism) or a microorganism that has been previously modified (e.g., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010, with Deutsche Sammlung von Mikroorganismen and Zellkulturen GmbH (DSMZ) located at Inhoffenstraß 7B, D-38124 Braunschweig, Germany on Jun. 7, 2010, under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*, *Clostridium ljungdahlii*, or *Clostridium ragsdalei*. In a preferred embodiment, the microorganism of the invention is derived from *Clostridium autoethanogenum* LZ1561, which is deposited under DSMZ accession number DSM23693.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert $CO$, $CO_2$, and/or $H_2$ to acetyl-CoA.

"C1" refers to a one-carbon molecule, for example, $CO$, $CO_2$, $CH_4$, or $CH_3OH$. "C1-oxygenate" refers to a one-carbon molecule that also comprises at least one oxygen atom, for example, $CO$, $CO_2$, or $CH_3OH$. "C1-carbon source" refers a one carbon-molecule that serves as a partial or sole carbon source for the microorganism of the invention. For example, a C1-carbon source may comprise one or more of $CO$, $CO_2$, $CH_4$, $CH_3OH$, or $CH_2O_2$. Preferably, the C1-carbon source comprises one or both of $CO$ and $CO_2$. A "C1-fixing microorganism" is a microorganism that has the ability to produce one or more products from a C1-carbon source. Typically, the microorganism of the invention is a C1-fixing bacterium.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the invention is an anaerobe.

"Acetogens" are obligately anaerobic bacteria that use the Wood-Ljungdahl pathway as their main mechanism for energy conservation and for the synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, NY, 2006). All naturally occurring acetogens are C1-fixing, anaerobic, autotrophic, and non-methanotrophic. Typically, the microorganism of the invention is an acetogen.

An "ethanologen" is a microorganism that produces or is capable of producing ethanol. Typically, the microorganism of the invention is an ethanologen.

An "autotroph" is a microorganism capable of growing in the absence of organic carbon. Instead, autotrophs use inorganic carbon sources, such as $CO$ and/or $CO_2$. Typically, the microorganism of the invention is an autotroph.

A "carboxydotroph" is a microorganism capable of utilizing CO as a sole source of carbon and energy. Typically, the microorganism of the invention is a carboxydotroph.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

"Substrate" refers to a carbon and/or energy source for the microorganism of the invention. Typically, the substrate is gaseous and comprises a C1-carbon source, for example, $CO$, $CO_2$, and/or $CH_4$. Preferably, the substrate comprises a C1-carbon source of $CO$ or $CO+CO_2$. The substrate may further comprise other non-carbon components, such as $H_2$ or $N_2$.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The microorganism of the invention may be cultured with gas to produce one or more products. For instance, the microorganism of the invention may produce or may be engineered to produce ethanol (WO 2007/117157), acetate (WO 2007/117157), 1-butanol (WO 2008/115080, WO 2012/053905, and WO 2017/0066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (MEK) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1 propanol (WO 2014/0369152 and WO 2017/0066498), 1-hexanol (WO 2017/0066498), 1-octanol (WO 2017/0066498), chorismate-derived products (WO 2016/191625), 3 hydroxybutyrate (WO 2017/066498), 1,3 butanediol (WO 2017/0066498), 2-hydroxyisobutyrate or 2-hydroxyisobutyric acid (WO 2017/0066498), isobutylene (WO 2017/0066498), adipic acid (WO 2017/0066498), 1,3 hexanediol (WO 2017/0066498), 3-methyl-2-butanol (WO 2017/0066498), 2-buten-1-ol (WO 2017/0066498), isovalerate (WO 2017/0066498), isoamyl alcohol (WO 2017/0066498), and monoethylene glycol (WO 2019/126400). In certain embodiments, microbial biomass itself may be considered a product. One or more of these products may be further converted to produce at least one component of diesel, jet fuel, and/or gasoline. Additionally, the microbial biomass may be further processed to produce at least a portion of a single cell protein (SCP).

A "single cell protein" (SCP) refers to a microbial biomass that may be used in protein-rich human and/or animal feeds, often replacing conventional sources of protein supplementation such as soymeal or fishmeal. To produce a single cell protein or other product, the process may comprise additional separation, processing, or treatments steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavor, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, $3^{rd}$ revision, pages 575-633, 2014.

"Selectivity" refers to the ratio of the production of a desired product to the production of all fermentation products produced by a microorganism. The microorganism of the invention may be engineered to produce products at a certain selectivity or at a minimum selectivity. In one embodiment, a desired product accounts for at least about 5%, 10%, 15%, 20%, 30%, 50%, 75%, or 85% of all fermentation products produced by the microorganism of the invention. In one embodiment, the desired product accounts for at least 10% of all fermentation products produced by the microorganism of the invention, such that the microorganism of the invention has a selectivity for the desired product of at least 10%. In another embodiment, the desired product accounts for at least 30% of all fermentation products produced by the microorganism of the invention, such that the microorganism of the invention has a selectivity for the desired product of at least 30%.

The fermentation should desirably be carried out under appropriate conditions for production of the desired product. Typically, the fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently the capital cost of the fermentation equipment.

The fermentation broth containing the desired product may be continuously removed from the bioreactor to effectuate product recovery. Desired products may be separated or purified from a fermentation broth using any suitable product recovery process, which may utilize a method or combination of methods known in the art, including, for example, fractional distillation, vacuum distillation, extractive distillation, evaporation, pervaporation, gas stripping, phase separation, and extractive fermentation, including, for example, liquid-liquid extraction. In certain embodiments, desired products are recovered from the fermentation broth by continuously removing a portion of the broth from the bioreactor, separating microbial cells from the broth (conveniently by filtration), and recovering one or more desired products from the broth. Alcohols and/or acetone may be recovered, for example, by distillation. Acids may be recovered, for example, by adsorption on activated charcoal. Separated microbial cells may be returned to the bioreactor. The cell-free permeate remaining after desired products have been removed may also be returned to the bioreactor. Additional nutrients may be added to the cell-free permeate to replenish the medium before it is returned to the bioreactor.

DESCRIPTION

The inventors found that by optimizing the usage and composition of the various gas streams, fermentation efficiency and overall carbon capture efficiency can be improved. By tailoring the composition of the gas stream being used by the fermentation process the inventors found that it is possible to enhance the production of certain desired products. In various instances the invention optimizes the flow of gas to parallel fermentation processes to improve product selectivity of desired products. In other instances the invention optimizes the flow of gas to fermentation processes in series to improve product selectivity of desired products. In various instances the composition of the gas being sent to a particular fermentation process is optimized to a particular $H_2$:CO ratio such that the gas is ideal for producing a particular fermentation product.

By using the hydrogen depleted gas the fermentation process may optimally produce one or more products selected from the group consisting of ethanol, acetate, monoethylene glycol (MEG), 1,2-propanediol, 3-hydroxypropionate, acetone, isopropanol, lactate, 1,3-butanediol, 2-butanol, 2-hydroxyisobutyric acid, 3-hydroxybutyrate, methyl ethyl ketone (MEK), isoamyl alcohol, terpenes including isoprene, adipic acid, 1-hexanol, 1-octanol, and chorismate-derived products. In certain instances, it is more advantageous to produce certain products with the hydrogen depleted stream instead of the hydrogen rich stream. Products such as 3-hydroxypropionate, isoamyl alcohol, and/or chorismate-derived products are preferably produced using the hydrogen depleted stream instead of the hydrogen rich stream.

The inventors found that by operating at least two fermentation processes, either in parallel or in series, the incoming feed gas can be separated into a hydrogen rich stream and a hydrogen depleted stream each of which are optimal for producing certain products in a gas fermentation process. In addition, when operating at least two fermentation processes in series, the first fermentation process can be optimized to produce acetic acid, which can then be converted in the second fermentation process to ethanol, resulting in higher overall production of ethanol. By using two fermentation processes, each operated to receive different streams, either hydrogen rich or hydrogen depleted, overall carbon capture efficiency can be improved as substantially all of the gas is utilized by at least one of the fermentation processes to produce at least one fermentation product instead of producing substantial amounts of unwanted by-products such as carbon dioxide.

At least a portion of the incoming feed gas may be sourced from a gasification process. In addition to utilizing the incoming feed gas for fermentation, in certain instances the inventors found it beneficial to use at least a portion of either vent gas from the fermentation process and/or at least a portion of the incoming gas stream from the gasification process to dry the feedstock used by the gasification process.

By utilizing at least a portion of the incoming gas stream from the gasification process and/or vent gas stream from the fermentation process to dry the feedstock for the gasification process, the efficiency of the gasification process can be improved. Specifically, the inventors found that use of vent gas or incoming gas to dry incoming municipal solid waste and/or biomass feedstock used in the gasification process results in increased energy efficiency, better syngas quality, and increased product revenue when compared to using vent gas for electricity or steam generation. The inventors found that use of vent gas for electricity or steam generation can, at best, recover sixty percent (60%) of the vent gas energy, forty percent (40%) from electricity and twenty percent (20%) from steam. In contrast, use of the vent gas for drying of feedstock can recover as much as ninety-two percent (92%) of the vent gas energy as improved yield in syngas.

As such when the industrial source is a gasification process it is more economic to use the vent gas for drying than to produce electricity or steam. The inventors found when the vent gas is used for drying municipal solid waste (MSW) instead of being used for steam or electricity generation, the value of the products produced from greater syngas generation exceeds the value of the electricity or steam that otherwise would have been generated. A comparison of expected revenue is provided in the below tables. Although this comparison is provided by assuming the fermentation process is ethanol, in various other instances when one or more other fermentation product is produced it may still be beneficial to use at least a portion of the vent gas for drying. The below chart showing the value of vent gas used in gasification is provided based upon the use of a 41.7 tonnes per hour (TPH) gasifier, fermentation unit with 1000 tonnes per day (TPD) feedstock, with a feedstock energy density of 11 MJ/kg.

| Vent Gas Used in Gasification | |
|---|---|
| Vent Gas | 50 GJ/h |
| Dryer Efficiency | 3 GJ/tonne water |
| Water Removed | 6.7 tonne/h |
| MSW Starting Moisture | 40% |
| MSW Final Moisture | 23% |
| Estimated Increase in Syngas Efficiency | 16.7% relative |
| Estimated Increases in Syngas Production | 45.9 GJ/h |
| Estimated Increases in Ethanol Production | 1.0 tonne/h |
| Value of Vent Gas at Ethanol Price of $1000/tonne | $20/GJ |

| Vent Gas Used in Electricity and Steam Generation | |
|---|---|
| Vent Gas | 50 GJ/h |
| Cogeneration Electricity Efficiency | 40% |
| Cogeneration Steam Efficiency | 20% |
| Estimated Electrical Output | 5.6 MW |
| Estimated Steam Output | 4.5 tonne/h |
| Value of Vent Gas at Electricity Price of $80/MWh and Steam Price of $20/tonne | $10.8/GJ |

As illustrated by the above tables, the value of the vent gas is higher when the vent gas is used for drying ($20/GJ) instead of being used for steam or electricity generation ($10.8/GJ). As such, in one or more embodiments, at least a portion of the vent gas is used by a feedstock drying process.

Figure 1:
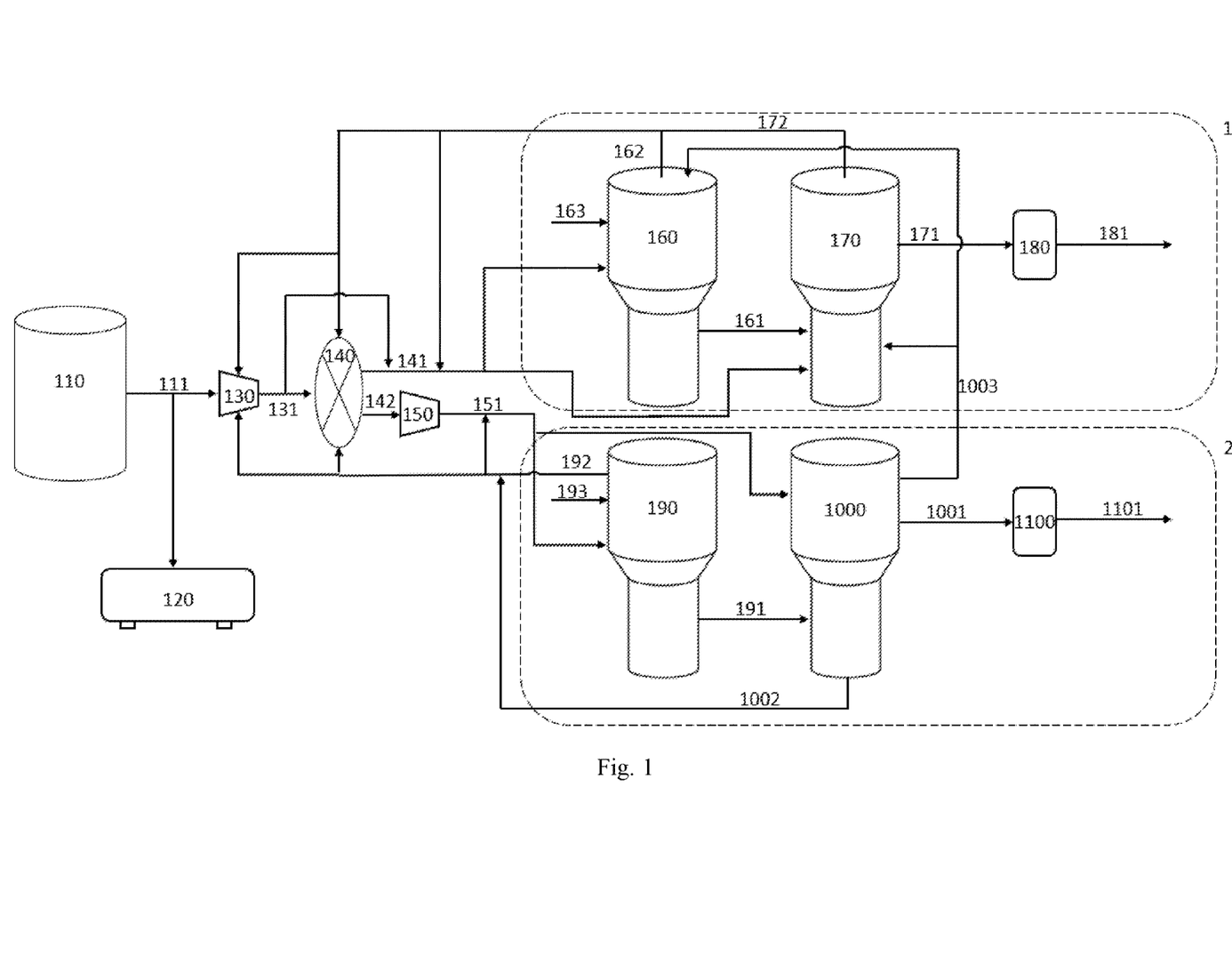
FIG. 1 shows a process integration scheme depicting parallel fermentation processes producing separate products from optimized gas streams, in accordance with one aspect of the invention.
Figure 2:
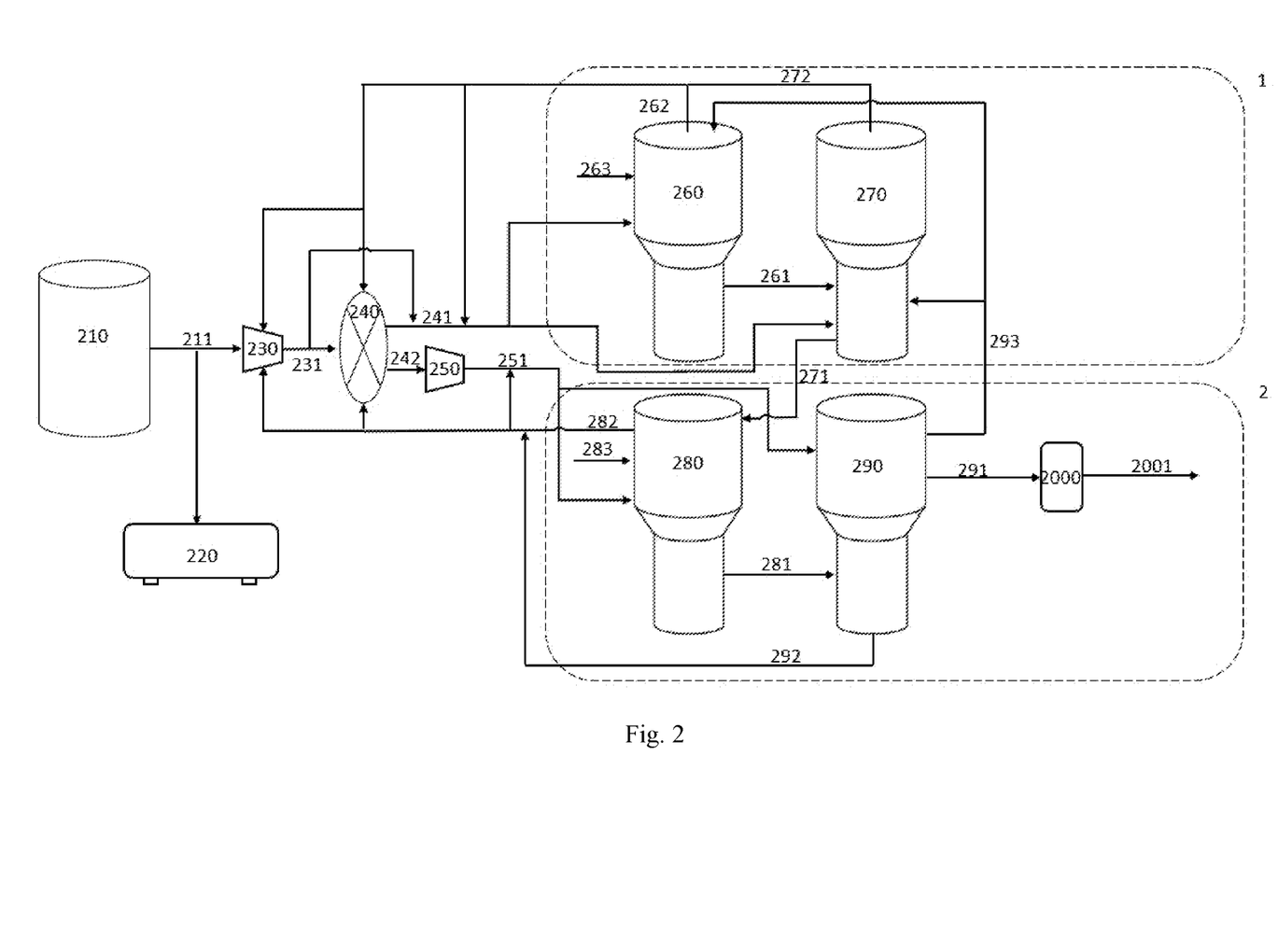
FIG. 2 shows a process integration scheme depicting the flow of optimized gas streams to fermentation processes in series, in accordance with one aspect of the invention.
Figure 3:
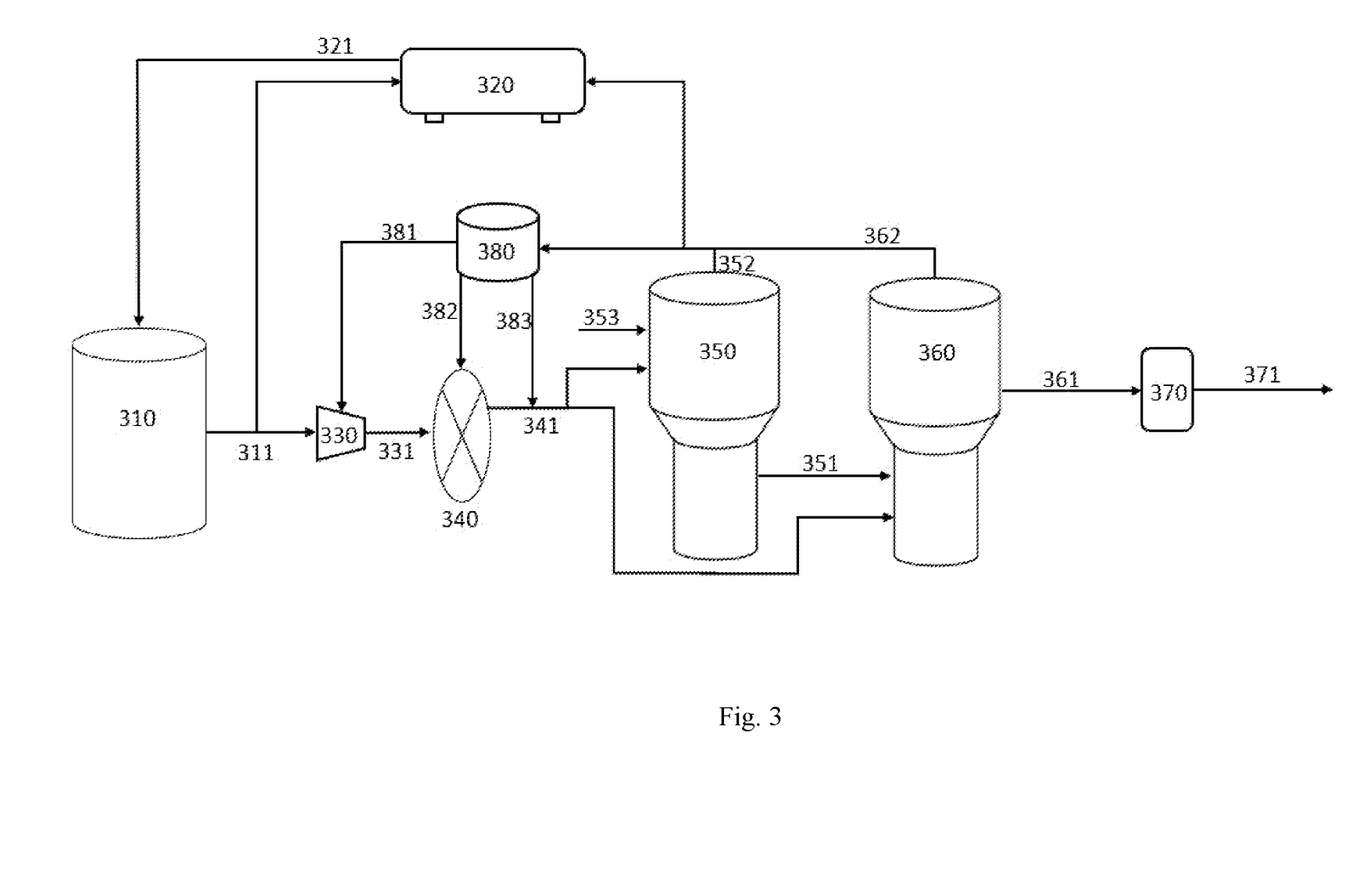
FIG. 3 shows a process integration scheme depicting the utilization of a recycled vent gas from the fermentation process in combination with a gas storage tank and a steam generator, electricity generator, and/or a feedstock drying process, in accordance with one aspect of the invention.

The aforementioned benefits are best achieved by controlling the usage and composition of the various gas streams as shown in FIGS. 1-3, described below.

FIG. 1 shows a process integration scheme depicting parallel fermentation processes 1, 2 producing separate products 171, 1001 from optimized gas streams 141, 142 in accordance with one aspect of the invention. In various instances, each fermentation process 1, 2 may be composed of at least two bioreactors 160, 170 and 190, 1000 in series. Preferably, the fermentation processes 1, 2 are integrated with at least one industrial source 110 such that each fermentation process 1, 2 is capable of receiving at least a portion of an optimized gas stream 141, 142 from the industrial source 110. Preferably, the gas stream 111 from the industrial source 110 is separated into a hydrogen rich stream 141 and a hydrogen depleted stream 142 using at least one hydrogen separation module 140. At least a portion of the hydrogen rich stream 141 is fermented in a first fermentation process 1 using at least one reactor 160 comprising a liquid nutrient medium containing a culture of one or more C1-fixing microorganism to produce a first fermentation product 171. In various instances, the first fermentation process 1 is comprised of two or more reactors 160, 170. At least a portion of the hydrogen depleted stream 142 is fermented in a second fermentation process 2 using at least one reactor 190 comprising a liquid nutrient medium containing a culture of one or more C1-fixing microorganism to produce a second fermentation product 1001. In various instances, the second fermentation process 2 is comprised of two or more reactors 190, 1000. Preferably the first fermentation product 171 produced by the first fermentation process 1 and the second fermentation product 1001 produced by the second fermentation process 2 are different products. In various instances the first fermentation product 171 is ethanol and the second fermentation product 1001 is 2,3-butandediol. In particular embodiments, liquid nutrient medium and process water 163, 193 are flowed to the first fermentation process 1 and second fermentation process 2 in parallel.

In certain instances the industrial source 110 is selected from the group consisting of carbohydrate fermentation, gas fermentation, cement making, pulp and paper making, steel making, oil refining and associated processes, petrochemical production, coke production, anaerobic or aerobic digestion, gasification, natural gas extraction, methane reformation, oil extraction, metallurgical processes, for production and/or refinement of aluminium, copper, and/or ferroalloys, geological reservoirs, and catalytic processes. In various instances, at least a portion of the gas stream 111 is comprised of blast furnace top gas from a metallurgical process 110. In various instances, at least a portion of the gas stream 111 is derived from a methane reformation process 110. The methane reformation process preferably converts at least a portion of a methane-containing gas into a gas stream 111 comprising at least a portion of carbon monoxide and hydrogen.

In certain instances the hydrogen separation module 140 is a pressure swing adsorption process. Preferably, the hydrogen separation module 140 is provided upstream of the fermentation processes 1, 2 so as to produce a hydrogen rich stream 141 and a hydrogen depleted stream 142 from an incoming gas 111 from the industrial source 110. In certain instances the incoming gas 111 is sent to one or more compressor 130 to increase the pressure of the incoming gas stream 111 and produce a pressurized incoming gas stream 131. When utilizing a pressure swing adsorption process as the hydrogen separation module 140, the hydrogen rich stream 141 exits the hydrogen separation module 140 at an increased pressure relative to the hydrogen depleted stream 142. As such, when utilizing a pressure swing adsorption process as the hydrogen separation module 140, the hydrogen depleted stream 142 is preferably sent to one or more compressor 150 to produce a pressurized hydrogen depleted stream 151 before being sent to the second fermentation process 2.

Preferably, when the first fermentation process 1 is comprised of multiple bioreactors 160, 170 the hydrogen rich stream 141 is sent to the bioreactors 160, 170 in parallel, and the fermentation broth 161 is sent in series from the first bioreactor 160 to the second bioreactor 170.

Preferably, when the second fermentation process is comprised of multiple bioreactors 190, 1000 the hydrogen depleted stream 142, which may be a pressurized hydrogen depleted stream 151, is sent to the bioreactors 190, 1000 in parallel and the fermentation broth 191 is sent in series from the first bioreactor 190 to the second bioreactor 1000.

To recover product 171 from the first fermentation process 1 one or more product recovery process 180 may be used. In certain instances the product recovery process 180 is capable of producing a purified product stream 181.

To recover product 1001 from the second fermentation process 2 one or more product recovery process 1100 may be used. In certain instances the product recovery process 1100 is capable of producing a purified product stream 1101.

The invention is capable of tailoring the composition of the gas being used by the fermentation processes 1, 2 so as to enhance the production of various products 171, 1001. One method of optimizing the composition of the gas being used by the fermentation processes 1, 2 is to utilize at least a portion of the vent gas 162, 172, 192, 1002 produced in the bioreactors 160, 170, 190, 1000. In certain instances at least a portion of the vent gas 162, 172 produced in the first fermentation process 1 is recycled to the hydrogen rich stream 141. At least a portion of the vent gas 162, 172 may be recycled either upstream of the hydrogen separation module 140, recycled into the hydrogen separation module 140, and/or recycled downstream of the hydrogen separation module 140 to optimize the composition of the gas being used by the first fermentation process 1. In certain instances at least a portion of the vent gas 192, 1002 produced in the second fermentation process 2 is recycled to the hydrogen depleted stream 151. At least a portion of the vent gas 192, 1002 may be recycled either upstream of the hydrogen separation module 140, recycled into the hydrogen separation module 140, and/or recycled downstream of the hydrogen separation module 140 to optimize the composition of the gas being used by the second fermentation process 2.

In various instances, the hydrogen rich stream 141 is optimized by blending at least a portion of the incoming gas stream 111, which may be a pressurized incoming gas stream 131, with the hydrogen rich stream 141 in order to meet minimum carbon monoxide requirements in the hydrogen rich stream 141.

When the incoming gas stream 111 from the industrial source 110 is in excess of what the fermentation processes 1, 2 can utilize, at least a portion of the incoming gas stream 111 may be used by a steam boiler, cogeneration unit, and/or feedstock drying process 120. Use of at least a portion of the incoming gas stream 111 in a feedstock drying process 120 is particularly useful when the incoming gas stream 110 is particularly dilute and would have poor efficiency for conversion to electricity. In various instances, when the industrial source 110 comprises one or more gasification process, at least a portion of the incoming gas stream 111 is used by a feedstock drying process 120, regardless of whether or not the gas is in excess of what the fermentation processes 1, 2 can utilize.

Preferably, the fermentation processes 1, 2 are able to operate in a continuous manner. To ensure that the fermentation processes 1, 2 are able to operate in a continuous manner the bioreactors 160, 170, 190, 1000 should preferably comprise an optimal proportion of viable microbes. In certain instances, use of carbon monoxide rich gas (otherwise known as hydrogen depleted gas 142) increases the relative proportion of microbial biomass produced by the fermentation process relative to the use of hydrogen rich gas 141. To maintain the culture within the first fermentation process 1, which utilizes hydrogen rich gas 141, at least a portion of the bleed stream 1003, comprising microbial biomass, may be sent from the bioreactors 190, 1000 of the second fermentation process 2 to the bioreactors 160, 170 of the first fermentation process 1. Preferably, at least a portion of the microbial biomass from the bioreactors 190, 1000 of the second fermentation process 2 is viable. In certain instances the use of the bleed stream 1003 from the second fermentation process 2 is completed in a continuous manner.

In various instances, the fermentation processes 1, 2 utilize one or more C1-fixing microorganism to ferment a C1-containing gas and produce one or more fermentation products 171, 1001. The C1-fixing microorganism used by the fermentation processes are preferably selected from the group consisting of *Moorella*, *Clostridium*, *Ruminococcus*, *Acetobacterium*, *Eubacterium*, *Butyribacterium*, *Oxobacter*, *Methanosarcina*, and *Desulfotomaculum*. Preferably, the C1-fixing microorganisms used by the fermentation processes 1, 2 is *Clostridium autoethanogenum*.

FIG. 2 shows a process integration scheme depicting the flow of optimized gas streams 241, 242 to fermentation processes 1, 2 in series in accordance with one aspect of the invention. In various instances, each fermentation process 1, 2 may be composed of at least two bioreactors 260, 270 and 280, 290 in series. Preferably, the fermentation processes 1, 2 are integrated with at least one industrial source 210 such that each fermentation process 1, 2 is capable of receiving at least a portion of an optimized gas stream 241, 242 from the industrial source 210. Preferably, the gas stream 211 from the industrial source 210 is separated into a hydrogen rich stream 241 and a hydrogen depleted stream 242 using at least one hydrogen separation module 240. At least a portion of the hydrogen rich stream 241 is fermented in a first fermentation process 1 using at least one reactor 260 comprising a liquid nutrient medium containing a culture of one or more C1-fixing microorganism to produce a first fermentation product 271. In various instances, the first fermentation process 1 is comprised of two or more reactors 260, 270. At least a portion of the hydrogen depleted stream 242 is fermented in a second fermentation process 2 using at least one reactor 280 comprising a liquid nutrient medium containing a culture of one or more C1-fixing microorganism to produce a second fermentation product 291. In various instances, the second fermentation process 2 is comprised of two or more reactors 280, 290. Preferably the first fermentation product 271 produced by the first fermentation process 1 and the second fermentation product 291 produced by the second fermentation process 2 are different products. In various instances the first fermentation product 271 is acetic acid and the second fermentation product 291 is ethanol. Preferably at least a portion of the acetic acid 271 from the first fermentation process 1 is passed to the second fermentation process 2 to convert at least a portion of the acetic acid 271 to ethanol 291. In particular embodiments, liquid nutrient medium and process water 263, 283 are flowed to the first fermentation process 1 and second fermentation process 2 in parallel.

In certain instances the industrial source 210 is selected from the group consisting of carbohydrate fermentation, gas fermentation, cement making, pulp and paper making, steel making, oil refining and associated processes, petrochemical production, coke production, anaerobic or aerobic digestion, gasification, natural gas extraction, methane reformation, oil extraction, metallurgical processes, for production and/or refinement of aluminium, copper, and/or ferroalloys, geological reservoirs, and catalytic processes. In various instances, at least a portion of the gas stream 211 is comprised of blast furnace top gas from a metallurgical process 210. In various instances, at least a portion of the gas stream 211 is derived from a methane reformation process 210. The methane reformation process 210 preferably converts at least a portion of a methane-containing gas into a gas stream 211 comprising at least a portion of carbon monoxide and hydrogen.

In certain instances the hydrogen separation module 240 is a pressure swing adsorption process. Preferably, the hydrogen separation module 240 is provided upstream of the fermentation processes 1, 2 so as to produce a hydrogen rich stream 241 and a hydrogen depleted stream 242 from an incoming gas 211 from the industrial source 210. In certain instances the incoming gas 211 is sent to one or more compressor 230 to increase the pressure of the incoming gas stream 211 and produce a pressurized incoming gas stream 231. When utilizing a pressure swing adsorption process as the hydrogen separation module 240, the hydrogen rich stream 241 exits the hydrogen separation module 240 at an increased pressure relative to the hydrogen depleted stream 242. As such, when utilizing a pressure swing adsorption process as the hydrogen separation module 240, the hydrogen depleted stream 242 is preferably sent to one or more compressor 250 to produce a pressurized hydrogen depleted stream 251 before being sent to the second fermentation process 2.

Preferably, when the first fermentation process 1 is comprised of multiple bioreactors 260, 270 the hydrogen rich stream 241 is sent to the bioreactors 260, 270 in parallel, and the fermentation broth 261 is sent in series from the first bioreactor 260 to the second bioreactor 270.

Preferably, when the second fermentation process is comprised of multiple bioreactors 280, 290 the hydrogen depleted stream 242, which may be a pressurized hydrogen depleted stream 251, is sent to the bioreactors 280, 290 in parallel and the fermentation broth 281 is sent in series from the first bioreactor 280 to the second bioreactor 290.

When the product of the first fermentation process 1 is sent to the second fermentation process 2 to produce a final product 291 one or more product recovery process 2000 may be used to recover a purified product stream 2001.

The invention is capable of tailoring the composition of the gas being used by the fermentation processes 1, 2 so as to enhance the production of various products 271, 291. One method of optimizing the composition of the gas being used by the fermentation processes 1, 2 is to utilize at least a portion of the vent gas 262, 272, 282, 292 produced in the bioreactors 260, 270, 280, 290. In certain instances at least a portion of the vent gas 262, 272 produced in the first fermentation process 1 is recycled to the hydrogen rich stream 241. At least a portion of the vent gas 262, 272 may be recycled either upstream of the hydrogen separation module 240, recycled into the hydrogen separation module 240, and/or recycled downstream of the hydrogen separation module 240 to optimize the composition of the gas being used by the first fermentation process 1. In certain instances at least a portion of the vent gas 282, 292 produced in the second fermentation process 2 is recycled to the hydrogen depleted stream 251. At least a portion of the vent gas 282, 292 may be recycled either upstream of the hydrogen separation module 240, recycled into the hydrogen separation module 240, and/or recycled downstream of the hydrogen separation module 240 to optimize the composition of the gas being used by the second fermentation process 2.

In various instances, the hydrogen rich stream 241 is optimized by blending at least a portion of the incoming gas stream 211, which may be a pressurized incoming gas stream 231, with the hydrogen rich stream 241 in order to meet minimum carbon monoxide requirements in the hydrogen rich stream 241.

When the incoming gas stream 211 from the industrial source 210 is in excess of what the fermentation processes 1, 2 can utilize, at least a portion of the incoming gas stream 211 may be used by a steam boiler, cogeneration unit, and/or feedstock drying process 220. Use of at least a portion of the incoming gas stream 211 in a feedstock drying process 220 is particularly useful when the incoming gas stream 210 is particularly dilute and would have poor efficiency for conversion to electricity. In various instances, when the industrial source 210 comprises one or more gasification process, at least a portion of the incoming gas stream 211 is used by a feedstock drying process 220, regardless of whether or not the gas is in excess of what the fermentation processes 1,2 can utilize.

Preferably, the fermentation processes 1, 2 are able to operate in a continuous manner. To ensure that the fermentation processes 1, 2 are able to operate in a continuous manner the bioreactors 260, 270, 280, 290 should preferably comprise an optimal proportion of viable microbes. In certain instances, use of carbon monoxide rich gas (otherwise known as hydrogen depleted gas 242) increases the relative proportion of microbial biomass produced by the fermentation process relative to the use of hydrogen rich gas 241. To maintain the culture within the first fermentation process 1, which utilizes hydrogen rich gas 241, at least a portion of the bleed stream 293, comprising microbial biomass, may be sent from the bioreactors 280, 290 of the second fermentation process 2 to the bioreactors 260, 270 of the first fermentation process 1. Preferably, at least a portion of the microbial biomass from the bioreactors 280, 290 of the second fermentation process 2 is viable. In certain instances the use of the bleed stream 293 from the second fermentation process 2 is completed in a continuous manner.

In various instances, the fermentation processes 1, 2 utilize one or more C1-fixing microorganism to ferment a C1-containing gas and produce one or more fermentation products 271, 291. The C1-fixing microorganism used by the fermentation processes are preferably selected from the group consisting of *Moorella, Clostridium, Ruminococcus, Acetobacterium, Eubacterium, Butyribacterium, Oxobacter, Methanosarcina*, and *Desulfotomaculum*. Preferably, the C1-fixing microorganism used by the fermentation processes 1, 2 is *Clostridium autoethanogenum*.

FIG. 3 shows a process integration scheme depicting the utilization of a recycled vent gas 352, 362 from the fermentation process in combination with a gas storage tank 380 and a steam generator, electricity generator, and/or a feedstock drying process 320, in accordance with one aspect of the invention. In certain instances, the recycling of at least a portion of the vent gas 352, 362 to the bioreactors 350, 360, reduces and/or mitigates the potential inhibition of the culture within the bioreactors 350, 360. In various instances, at least a portion of the vent gas 352, 362 is sent to a gas storage tank 380 prior to being utilized. Preferably, when being utilized, at least a portion of the vent gas 352, 362 from the storage tank 380 can be sent upstream 381 of the pressure swing adsorption process 340, into 382 the pressure swing adsorption process 340, or downstream 383 of the pressure swing adsorption process 340. In certain instances, at least a portion of the vent gas 352, 362 is sent to the steam generator, electricity generator, and/or feedstock drying process 320 in addition to, or in replacement of, being recycled to the bioreactors 350, 360.

Preferably, at least a portion of the vent gas 352, 362 is passed through a pressure swing adsorption process 340 prior to being recycled back to the bioreactors 350, 360. In various instances, at least a portion of the vent gas 352, 262 is sent to the gas storage tank 380 prior to being passed to the pressure swing adsorption process 340. The pressure swing adsorption process 340 was found particularly useful to remove a variety of components from the gas stream 311, which may be pressurized 331 if passed through a compressor 330, and/or the vent gas stream 352, 362. The pressure swing adsorption process 340 was found to remove at least a portion of at least one component selected from the group consisting of carbon dioxide, inorganic hydrocarbons, tars, organic nitrogen, and organic and inorganic sulfur from the gas stream 311 and/or the vent gas stream 352, 362 to produce a clarified vent gas 341. In various instances, the pressure swing adsorption process 340 was found to simultaneously remove at least two components selected from the group consisting of carbon dioxide, inorganic hydrocarbons, tars, organic nitrogen, and organic and inorganic sulfur from the gas stream 311 and/or the vent gas stream 352, 362.

In certain instances, recycling of at least a portion of the vent gas 352, 362 to the bioreactors 350, 360 increases an overall composition of methane and nitrogen in the total gas stream 341 by at least fifteen percent (15%).

In various instances, recycling of at least a portion of the vent gas 352, 362 to the bioreactors 350, 360 increases an overall composition of methane and nitrogen in the total gas stream 341 by at least fifty percent (50%).

Increasing the proportion of inert gases such as methane and nitrogen was found to help mitigate the inhibition of the culture which may be seen when carbon monoxide composition is too high in the gas stream.

The fermentation process is preferably optimized to produce products 361 from a gas stream 311 from an industrial source 310. When including multiple bioreactors 350, 360 in series, the gas stream 331, which may be either hydrogen rich or hydrogen depleted, is preferably sent in parallel, the liquid nutrient medium and process water 353 are preferably sent to the first bioreactor 350, and the fermentation broth 351 is preferably sent from the first bioreactor 350 to the second bioreactor 360. Preferably, the products 361 produced by the fermentation process are separated using a one or more product recovery process 370 to produce a purified product stream 371.

At least a portion of the incoming gas stream 311 may be used by a steam boiler, cogeneration unit, and/or feedstock drying process 320 when the gas stream 311 from the industrial source 310 is in excess of what the fermentation process is capable of utilizing. However, in various instances, at least a portion of the incoming gas stream 311 is used by a feedstock drying process 320, regardless of whether or not the gas is in excess of what the fermentation process can utilize. Use of at least a portion of the gas stream 311 by the feedstock drying process 320 is particularly useful to produce a dried feedstock 321 for the gasification process. Drying the feedstock 321 for the gasification process was found to increase the efficiency of the gasification process 310.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavor in any country.

The use of the terms "a" and "an" and "the" and similar referents in the context of describing the invention (especially in the context of the following claims) are to be construed to cover both the singular and the plural unless otherwise indicated herein or clearly contradicted by context. The terms "comprising," "having," "including," and "containing" are to be construed as open-ended terms (e.g., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein is merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for optimizing the flow of gas to parallel fermentation processes, the method comprising:

a) separating a gas stream derived from at least one industrial source into a hydrogen rich stream and a hydrogen depleted stream using at least one hydrogen separation module;
    b) passing the hydrogen rich stream and hydrogen depleted stream in parallel to a first and second fermentation process respectively said first and second fermentation processes being run in parallel;
    c) fermenting at least a portion of the hydrogen rich stream in the first fermentation process using at least one reactor comprising a liquid nutrient medium containing a culture of at least one C1-fixing microorganism to produce a first fermentation product; and
    d) fermenting at least a portion of the hydrogen depleted stream in the second fermentation process comprising at least one reactor comprising a liquid nutrient medium containing a culture of at least one C1-fixing microorganism to produce a second fermentation product, wherein the first fermentation product and the second fermentation product are different products.

2. The method of claim 1, wherein the first fermentation product is ethanol and the second fermentation product is 2,3-butanediol.

3. The method of claim 1, wherein the liquid nutrient medium is flowed to the first fermentation process and the second fermentation process in parallel.

4. The method of claim 1, wherein the hydrogen separation module is a pressure swing adsorption process.

5. The method of claim 1, wherein the industrial source is selected from the group consisting of carbohydrate fermentation, gas fermentation, cement making, pulp and paper making, steel making, oil refining processes, petrochemical production, coke production, anaerobic digestion, aerobic digestion, gasification, natural gas extraction, methane reformation, oil extraction, metallurgical processes for production or refinement of aluminium, copper, or ferroalloys, geological reservoirs, catalyst regeneration, steam naphtha reforming, and any combination thereof.

6. The method of claim 1, wherein at least a portion of the gas stream is comprised of a blast furnace top gas from a metallurgical process.

7. The method of claim 1, further characterized in that at least a portion of a vent gas produced in the first fermentation process is recycled to the hydrogen rich stream.

8. The method of claim 7, wherein at least a portion of the vent gas produced in the first fermentation process is passed through a pressure swing adsorption process prior to being recycled to the hydrogen rich stream.

9. The method of claim 1, further characterized in that at least a portion of a vent gas produced in the second fermentation process is recycled to the hydrogen depleted stream.

10. The method of claim 9, wherein at least a portion of the vent gas produced in the second fermentation process is passed through a pressure swing adsorption process prior to being recycled to the hydrogen depleted stream.

11. The method of claim 1, wherein the at least one C1-fixing microorganism is selected from the group consisting of *Moorella*, *Clostridium*, *Ruminococcus*, *Acetobacterium*, *Eubacterium*, *Butyribacterium*, *Oxobacter*, *Methanosarcina*, and *Desulfotomaculum*.

12. The method of claim 1, wherein the C1-fixing microorganism is *Clostridium autoethanogenum*.

13. The method of claim 1, wherein at least a portion of the gas stream is derived from a methane reformation process.

\* \* \* \* \*